United States Patent
Petignaud et al.

(10) Patent No.: US 10,234,700 B2
(45) Date of Patent: Mar. 19, 2019

(54) METHOD FOR CHECKING THE CORRECT ASSEMBLY OF A FRAME AND CORRECTIVE LENSES

(71) Applicant: ESSILOR INTERNATIONAL (COMPAGNIE GENERALE D'OPTIQUE), Charenton-le-Pont (FR)

(72) Inventors: Cécile Petignaud, Villejuif (FR); Thierry Laloux, Paris (FR); Nacer Lakhchaf, Creil (FR); Benjamin Rousseau, Villiers-sur-orge (FR); Marie-Anne Berthezene, Maison-alfort (FR)

(73) Assignee: ESSILOR INTERNATIONAL (COMPAGNIE GENERALE D'OPTIQUE), Charenton-le-pont (FR)

( * ) Notice: Subject to any disclaimer, the term of this patent is extended or adjusted under 35 U.S.C. 154(b) by 0 days.

(21) Appl. No.: 15/105,225

(22) PCT Filed: Dec. 3, 2014

(86) PCT No.: PCT/FR2014/053146
§ 371 (c)(1),
(2) Date: Jun. 16, 2016

(87) PCT Pub. No.: WO2015/092194
PCT Pub. Date: Jun. 25, 2015

(65) Prior Publication Data
US 2017/0003523 A1 Jan. 5, 2017

(30) Foreign Application Priority Data
Dec. 16, 2013 (FR) ...................................... 13 62717

(51) Int. Cl.
*G02C 13/00* (2006.01)
*A61B 3/00* (2006.01)
*A61B 3/11* (2006.01)

(52) U.S. Cl.
CPC .......... *G02C 13/005* (2013.01); *A61B 3/0025* (2013.01); *A61B 3/111* (2013.01)

(58) Field of Classification Search
CPC ...... G02C 13/005; A61B 3/111; A61B 3/0025
USPC ........................................................ 351/204
See application file for complete search history.

(56) References Cited

U.S. PATENT DOCUMENTS

2011/0007269 A1    1/2011   Trumm et al.

FOREIGN PATENT DOCUMENTS

| FR | 2896682 | 8/2007 |
| FR | 2914173 | 10/2008 |
| FR | 2980592 | 3/2013 |
| WO | WO1999/001791 | 1/1999 |

*Primary Examiner* — Jack Dinh
(74) *Attorney, Agent, or Firm* — Norton Rose Fulbright US LLP

(57) ABSTRACT

The invention relates to a method for checking the correct assembly of a device consisting of a frame and of two corrective ophthalmic lenses. The main feature of a method according to the invention is that it includes the following steps: an initial step of determining at least one parameter which makes it possible to position the lenses in the frame relative to the face; a subsequent step of acquiring at least one image of the face of said wearer with said device, which shows centering and horizontal level marks; a step of comparing said at least one parameter determined during said initial step with the corresponding parameter deduced from said at least one image; and a step of making a decision regarding the correct assembly of the device.

14 Claims, No Drawings

METHOD FOR CHECKING THE CORRECT ASSEMBLY OF A FRAME AND CORRECTIVE LENSES

CROSS-REFERENCE TO RELATED APPLICATIONS

This application is a national phase application under 35 U.S.C. § 371 of International Application No. PCT/FR2014/053146 filed 3 Dec. 2014, which claims priority to French Patent Application No. 1362717 filed 16 Dec. 2013. The entire contents of each of the abovereferenced disclosures is specifically incorporated by reference herein without disclaimer.

The invention relates to a method for checking the fitting conformity of a frame and corrective eyeglasses. Generally, such a method is employed on delivery of a frame equipped with corrective eyeglasses, after morpho-geometric parameters of the wearer have been determined in a prior measurement-capture step carried out either by an optician or by the wearer himself.

Currently, this prior measurement-capture step is performed by an optician by means of various pieces of equipment, possibly for example consisting of a pupillometer measuring corneal reflections to determine interpupillary distance, a ruler and a measurer of pupillary height. Once these main parameters have been evaluated, a frame with suitable corrective eyeglasses is ordered, then delivered. The optician commonly uses a centering chart and a ruler to check the centering of the eyeglasses in the piece of equipment. The horizontality of the micro-circles is evaluated visually. These checks may be carried out either autonomously on the piece of equipment alone, or on the piece of equipment when the latter is in functional position on an individual.

A major drawback of this checking method is that certain measurements are subjective because they depend on the optician and are subject to parallax effects that increase the uncertainty in said measurements. When a measuring means is used, it has its own frame of reference, which may be different from another measuring means used, increasing a little more the sources of errors in the measurements. Lastly, the measurements performed in the prior step and that allow those characteristics of the face of the wearer which are required for the complete piece of equipment, comprising frame and eyeglasses, to be produced, to be determined, also depend on the posture of the person during said measurements. In other words, existing checking methods involve a certain number of approximations, liable to multiply the sources of error and therefore to bias the diagnosis of the fitting conformity of the frame and corrective eyeglasses.

Methods for checking the fitting conformity of a piece of equipment, composed of a frame and corrective eyeglasses, according to the invention allow a clear and realistic diagnosis to be provided by obviating the drawbacks of the prior art.

One subject of the invention is a method for checking the fitting conformity of a piece of equipment composed of a frame and two corrective ophthalmic eyeglasses.

The main feature of a method according to the invention is that it comprises the following steps:

An upstream step of determining at least one parameter allowing the eyeglasses to be positioned in the frame and relative to the face;

A downstream step of acquiring at least one image of the face of said wearer with said piece of equipment in which appear centering and horizontality reference marks;

A step of comparing said at least one parameter determined in said upstream step and the corresponding parameter deduced from said at least one image; and A step of reaching a decision on the fitting conformity of the piece of equipment.

The principle of such a checking method is based on objective measurements, performed on the basis of at least one image of the face of a wearer with the piece of equipment composed of the frame and the two corrective eyeglasses, said piece of equipment being provided with centering and horizontality reference marks in order to facilitate a reliable and rapid evaluation of fitting conformity. Preferably, once the conformity of the fit has been verified, these reference marks may be easily removed from said piece of equipment. These reference marks may for example be lines on the eyeglasses, indicating the location of the fitting crosses and/or a horizontal axis, said lines possibly being produced by means of a felt pen. The upstream step may be carried out, either by means of specific techniques involving various suitable apparatuses, or on the basis of the acquisition of at least one image of the face of the wearer with a frame bought by the wearer or a frame of identical reference without corrective eyeglasses. The comparing step allows any deviation that there might be between each parameter determined in the upstream step and each parameter deduced in the downstream step to be evaluated. The terms "upstream" and "downstream" are to be interpreted relative to time, the upstream step thus preceding the downstream step. According to one variant embodiment of a checking method according to the invention, the upstream measuring step and the downstream step are merged. Specifically, in the image of the downstream step, it is possible to view both the centering and horizontality reference marks of the downstream step, and the parameters that are determined during the upstream step. The comparison is therefore made in the image of the downstream step. To be complete, a checking method according to the invention must include a concluding step making it possible to take a clear stance with regard to the fitting conformity of the frame and corrective eyeglasses. This step of reaching a decision may be performed either rigorously and objectively with reference to predetermined reference deviations in each parameter, or by simply viewing the image acquired in the downstream step.

Preferably, the upstream step is carried out by means of the acquisition of at least one image of the face of the wearer with a frame without the corrective eyeglasses. In this way, the upstream step and the downstream step are carried out according to the same principle and allow the step of comparing each parameter to be facilitated by limiting the sources of error due to completely different operating conditions.

Preferably, the upstream step and the downstream step are carried out with the same operating mode and with identical measuring means. This method configuration further simplifies the step of comparing each parameter, by removing those sources of error which are related to differences in the conditions of implementation of the upstream step and downstream step, and to the use of different measuring means possibly for example possessing distinct calibrations.

Advantageously, when the upstream step and the downstream step are carried out in different frames of reference, said method comprises a step of readjusting parameters in order to allow the comparing step to be performed. Specifically, if different frames of reference, associated with the intrinsic properties of the apparatuses and items employed to perform the upstream step and the downstream step, are used, it is essential to apply a correction to certain values of the determined parameters, in order to convert all the values of the parameters to the same frame of reference, and thus make the comparing step reliable.

Advantageously, a method according to the invention comprises a step of checking the posture of the wearer between the upstream step and the downstream step, in order to make certain that the relative positions between the piece of equipment and the wearer are substantially identical in said two steps. Specifically, the relative position of the piece of equipment, which is composed in one case by the frame and the corrective eyeglasses and in the other case by the frame without corrective eyeglasses, must not be too different between the upstream step and the downstream step, as otherwise an additional and significant source of errors that will possibly bias the diagnosis will be introduced.

Preferably, the comparing step applies to at least one geometrico-morphological parameter chosen from the height, the pantoscopic angle, the horizontality of the frame, the horizontality of the eyeglasses relative to said frame, pupillary distance, the face-form angle of said frame and the position of the centering reference marks on each of the eyeglasses.

Preferably, a checking method according to the invention comprises a step of validating the conformity of the piece of equipment composed of the frame equipped with the corrective eyeglasses, integrating tolerance thresholds into the measurements. Specifically, even if there are deviations in the values of the parameters determined in the upstream step and those measured in the downstream step, this does not necessarily mean that the fit of the frame and corrective eyeglasses is not in conformity. It is therefore important to be able to define ranges of values in which the deviation between the parameters will be able to be considered not to be significant and that will therefore allow the fitting conformity of the piece of equipment to be validated.

Advantageously, a checking method according to the invention comprises a step of presentation of the validation of the conformity, by means of at least one image of the face of the wearer with the corrective-eyeglass frame and at least one piece of information visible on said image. A checking method according to the invention must be completed by providing the wearer with clear and user-friendly information on the fitting conformity of the frame and corrective eyeglasses. Such a method is not constraining insofar as it does not oblige the wearer to perform any action to obtain the diagnosis on the conformity of said fit. The information may for example appear in the form of a color, green if in conformity or red otherwise, or the form of any other distinctive symbol allowing the validation to be read without ambiguity.

Advantageously, a checking method according to the invention comprises a step of consulting a database in which appears, for an identified wearer and identified measuring means, the parameters determined in the upstream step, the operating conditions under which said parameters were obtained and the type of measuring means used, said base being made accessible to each of said wearers by means of an identifier. Specifically, since certain geometrico-morphological characteristics of the face of a wearer such as the pupillary distance change very little over time, it is desirable not to have to repeat the upstream step each time the wearer wants to change frame and/or corrective eyeglasses, this type of step always constituting a constraint.

Preferably, a checking method according to the invention comprises a step of adjusting the measurement. This step allows the person who carries out the downstream step, whether he is the wearer or the optician, to be informed that the result of the measurement will not be exploitable to validate the fitting conformity of the frame and corrective eyeglasses. This step may consist of an invitation to modify in real time the operating conditions. Once this step of adjusting the measurement has been performed, the measurements of the upstream step and those of the downstream step may be compared. If these measurements reveal a deviation larger than a threshold value, then an alarm is signalled.

According to one preferred embodiment of a checking method according to the invention, the upstream and downstream steps are carried out by the wearer with means equipped with a screen and connected to a telecommunications network. For this checking-method configuration, the wearer himself performs, without the assistance of an optician, the various steps of said method. Specifically, there currently exists a wide range of portable electronic means, including computers, telephones, or tablets, that are equipped with a camera and/or a webcam allowing the various steps of a checking method according to the invention to be carried out. The telecommunications network advantageously consists of the Internet.

Preferably, the downstream step, the comparing step and the validating step are carried out on a dedicated Internet site. This site may for example belong to a frame manufacturer or an eyeglass manufacturer, or to an organization the activity of which is directly related to the correction of the sight of an individual. Said site may also propose a user-friendly way, carried out by means of various actions to be undertaken by the wearer, of obtaining a validation of the fitting conformity of the frame and corrective eyeglasses. One typical type of action that a wearer could carry out consists in him positioning his face in front of the screen of a piece of electronic equipment equipped with a webcam, in a predefined frame on said screen, and in him acquiring various images with and without the frame and waiting for the verdict.

Advantageously, the downstream step, the comparing step and the validating step are performed on the basis of a display on the screen during the capture of images and of an instruction indicating to him how to modify his posture with the aim of minimizing errors during the comparing step.

Advantageously, the step of reaching a decision on the fitting conformity comprises a step of inspecting the position of distinctive reference marks on the corrective eyeglasses, said inspecting step being performed with an individual wearing the fitted piece of equipment.

Preferably, each distinctive reference mark is a cross affixed to each eyeglass of the piece of equipment, said crosses being supposed to indicate the position of the eyes of the individual. These crosses may, for example, be temporarily affixed to the eyeglasses before being removed once the checking step has been carried out. The checking step is performed with a certain tolerance, a minimum divergence in the positions of the crosses and the eyes of the individual possibly being accepted to obtain a positive diagnosis of the fitting conformity of the piece of equipment. This minimum divergence must however remain below a predetermined threshold value.

A second subject of the invention is a checking device for carrying out a checking method according to the invention.

The main feature of a checking device according to the invention is that it comprises means for acquiring and processing at least one image, measuring means for determining at least one parameter in the upstream step, scaling means, inspecting means, comparing means and means for displaying at least one piece of information on the validation of the fitting conformity of the frame.

Advantageously, a checking device according to the invention comprises a screen for viewing the face of the wearer with a frame and for displaying at least one piece of information on the validation of the fitting conformity of the frame with the corrective eyeglasses.

Preferably, the scaling means consists of at least one reference element of known size in said image. This reference element may be either obtained by virtue for example of an identifiable marking and/or a worn clip, or directly on the basis of corneal reflections.

Methods for checking the fitting conformity of a frame and corrective eyeglasses according to the invention have the advantage of being easy and rapid to implement and of not forcing the wearer to adopt constraining postures. In addition they have the advantage of providing a validation of the fitting conformity that is trustworthy and reliable, because of the objective character of the measurements which depend neither on an optician or on said wearer. Lastly, they have the advantage of being user-friendly, as they include a step of displaying on the screen a diagnosis of conformity that may be read and interpreted without ambiguity.

Below, a detailed description is given of various preferred embodiments of a method for checking the fitting conformity of a frame and two corrective eyeglasses according to the invention.

Generally, an individual seeking to equip himself with a frame and corrective eyeglasses goes to an optician with the prescription of an ophthalmologist specifying the optical characteristics of the corrective eyeglasses to be fitted. The optician then determines, by means of measurements and/or calculations, a certain number of morpho-geometric parameters of the face of this individual, such as for example his pupillary distances, in order to be able to dimension with the highest possible precision said frame and said corrective eyeglasses. Once the frame and said corrective eyeglasses have been delivered fitted, it is indispensable to verify the quality of this fit to be certain that the piece of equipment thus delivered is in conformity with the morpho-geometric parameters determined beforehand and that therefore there is no risk of an approximate or even defective fit causing the wearer any trouble.

Two configurations will be discussed: one in which the method is conducted in an optician's in the presence of an optician, and the other in which the method is conducted remotely in the presence only of the wearer.

The configuration in which the method according to the invention is conducted at an optician's will be discussed first.

Let us first assume that the optician possesses an image-capturing apparatus and a screen for viewing each of said images.

The upstream step of the method may for example serve to determine the height or heights of the eye rotation centers ERC and the monocular pupillary distances. Thus, to measure these two parameters:

the person puts on the chosen frame, which the optician has taken care to adjust, at this stage, without corrective eyeglasses.

a system allowing a calibration of size and of qualification of the inclination to be delivered is present in an image corresponding to a photo taken face-on, said system possibly for example being a "Visioffice" type clip.

the optician asks the person to adopt a reference position, possibly for example a primary position (position in which the person stands comfortably and facing straight ahead) or a specific known posture such as that adopted when driving or reading. This position concerns only the position of the head.

the heights and monocular pupillary distances may then be determined in two different ways: either by a direct measurement in the photo taken face-on, or by a measurement such as that advocated in patent FR2914173.

in both cases, the values that will serve to center the eyeglasses in the frame, both horizontally via the distances of the eye rotation centers ERC or the pupillary distances, and vertically via the height of the center of the pupils, are obtained.

The downstream measuring step will be carried out on the wearer with the frame and corrective eyeglasses delivered. This step is conducted as follows:

the optician hands to his customer the complete piece of equipment composed of the adjusted frame and the two corrective eyeglasses;

a reference mark of the eyeglass is accessible in an image corresponding to a photo taken face-on of the face of the wearer with the delivered piece of equipment, said reference mark possibly for example consisting of characteristic points of the frame marked with a felt tip;

the same system as that used in the downstream step, allowing a calibration of size and of qualification of the inclination to be delivered, is present in the image corresponding to a photo taken face-on. According to one variant embodiment, a clip may also be used provided that the dimensions thereof are known;

the optician asks his customer to position himself in the reference position, as in the preceding upstream step;

then asks him to look straight ahead;

the optician takes a photo or records a film.

The step of comparing the parameters of the upstream step and downstream step is carried out by means of image processing, this processing allowing the felt-tip marks on the eyeglass, and therefore the position of these marks in the frame, and also either the corneal reflections of the two eyes, or the pupil centers of the two eyes, to be located. The objective of this image processing is to verify that the fitting cross highlighted in felt tip is indeed superposed on the corneal reflections, or on the center(s) of the pupil(s) of the two eyes.

Let us secondly assume that the optician possesses a "Visioffice" type apparatus or another apparatus such as a video camera or camera.

The upstream step, allowing the height(s) of the eye rotation centers ERC and the monocular pupillary distances to be determined is conducted as follows:

the person puts on the chosen frame, which the optician has taken care to adjust, without its corrective eyeglasses;

a clip is placed on the frame of the person in order to give indications of dimensions, inclination and the posture of the wearer;

the optician asks the person to position himself in primary position;

the heights and monocular pupillary distances may then be determined by a direct measurement in the photo taken face-on;

the heights of the pupillary points of each of the two eyes from the lower edge of the frame and the monocular pupillary distances are obtained.

The downstream measuring step will be carried out on the wearer with the frame and corrective eyeglasses delivered. This step is conducted as follows:

the optician hands to his customer the complete piece of equipment composed of the adjusted frame and the two corrective ophthalmic eyeglasses;

the characteristic points of the fit of the glass in the frame are indicated on the eyeglass for example in felt tip;

the same clip as that used in the upstream step is placed on the frame in order to give indications of dimensions and inclination. It is not absolutely necessary to use the same clip. In the case where a different clip is used, it is enough to know its dimensions;

the optician asks his customer to position himself in primary position, as in the preceding upstream step;

then asks him to look straight ahead;

a photo or film is taken.

If needs be, the optician may ask the wearer to modify his posture in order to make it possible to pass to the comparing step.

The step of comparing the parameters of the upstream step and downstream step is carried out by means of image processing, this processing allowing the felt-tip marks on the eyeglass, and therefore the position of these marks in the frame, and also either the corneal reflections of the two eyes, or the pupil centers of the two eyes, to be located. The objective of this image processing is to verify that the fitting cross highlighted in felt tip is indeed superposed on the corneal reflections, or on the pupil center.

Let us thirdly assume that the optician possesses a complete system for measuring posture, for example of the OptiTrack or Natural Point type, and that the posture of the customer is checked.

When the optician asks the person to position himself in a reference position, in the upstream step, it is recommended to take a measurement of the posture adopted by the subject. This measurement may be performed by means or one or more photos or by acquiring a video. To guarantee a better precision of the acquisition of the primary posture of the wearer, markers are added to the head of said wearer and to the top of his body, said markers being independent of the frame. The optician may thus produce a photo or a video of elements of the top of the body of the person during the measurement capture, which will allow the position and orientation of the markers to be determined in a frame of reference associated with the place and therefore with the posture of the person. It is also possible to use a system for measuring posture via infrared radiation (such as for example the OptiTrack or Natural Point systems). One alternative solution consists in not using markers and in doing the image processing while taking as reference morphological reference elements of the face.

In the downstream step of measuring parameters with the frame and corrective eyeglasses, it is important to guarantee that the wearer is in an identical posture to that adopted in the upstream step, and in particular to guarantee an identical primary position, so that the step of comparing the parameters determined in the upstream step and the parameters measured in the downstream step is carried out credibly, without introducing additional sources of errors. For this downstream step, posture is determined with the same means as those used in the upstream step, thus allowing the wearer to correct his posture in real time in order to make it identical to that adopted in the upstream step. The wearer may be incited to correct his posture by means of an interface of the measuring system, or by instructions given by the optician, who indicates the movements to make to resume the right position.

The configuration in which the method according to the invention is carried out remotely by the wearer himself, for example by means of a video camera or a webcam, will now be discussed.

The upstream step of the method may for example serve to determine the fitting height, which is the distance between the center of the pupil and the lower frame edge, and the monocular pupillary distances. Thus, to measure these two parameters:

the wearer possibly adjusts the chosen frame on his face according to delivered recommendations, the wearer, wearing the chosen frame equipped with a clip or a system for calibrating size, places himself in front of the video camera or the webcam. The wearer may thus be sitting or standing. He may fixate a precise point or fixate a succession of various points that are determined so that the position of the subject is as natural as possible, the pupillary distances and fitting heights are then determined by processing one or more optionally averaged captured images.

At this stage of the method, an optician present on site or remotely interprets the captured images and adjusts if necessary the fitting heights. For example, if it is necessary and possible to adjust the frame, for example when it is equipped with adjustable nose pads, the optician may advocate adjusting these nose pads in the fitting phase, and in this case, he may increase or decrease the measured fitting height.

The downstream measuring step will be carried out on the wearer with the frame and corrective eyeglasses delivered. This step is conducted as follows:

The wearer puts on the frame equipped with its corrective eyeglasses, and optionally with the clip or the system for calibrating size of the downstream step, the frame having been adjusted by the wearer himself or during the fitting of the eyeglasses by the manufacturer.

The characteristic points of the eyeglasses represented by the micro-circles and the centering crosses may be highlighted on the eyeglasses. They are not highlighted on said eyeglasses if their position in the frame is considered to be known.

The one or more image captures are carried out by the wearer according to the same protocol as in the upstream step.

The step of comparing the parameters of the upstream step and downstream step is carried out by means of image processing, this processing allowing the juxtaposition of the fitting crosses and the center of the pupils of the two eyes to be checked.

Let us now assume not only that the method according to the invention is carried out remotely by the wearer himself, for example by means of a video camera or a webcam, but that the posture of said wearer is checked.

In order to limit the sources of error, it is recommended for the wearer to adopt the same posture in the upstream step of determining parameters and in the downstream step of measuring said parameters.

If it is assumed that the direction of the gaze of the wearer in the upstream determining step and in the downstream measuring step is indeed the same because said wearer is looking at the same target, it however remains important to ensure that the head of the wearer is in the same position and has the same orientation, with respect to the measuring and displaying system.

It is therefore recommended to take a measurement of the posture adopted by the wearer. This measurement may be performed by means of one or more photos or by acquiring a video. To guarantee a better precision of the acquisition of the primary posture of the wearer, markers are added to the head of said wearer and to the top of his body, said markers being independent of the frame. These markers may be printed by the wearer or may be ordered from an enterprise or a specialized organization. It thus becomes possible to acquire the position and orientation of elements of the top of the body of the person during the measurement capture. One alternative solution consists in not using markers and in doing the image processing while taking as reference morphological reference elements of the face.

For the downstream measuring step, it is necessary to guarantee that the video camera or webcam is positioned exactly in the same location as in the upstream measurement-capture step. To achieve this identical position, a validation/calibration phase may be envisioned with an object of known size, such as for example a bank card, in the measuring field.

In the downstream step of measuring parameters with the frame and corrective eyeglasses, it is important to guarantee that the wearer is in an identical posture to that adopted in the upstream step, and in particular to guarantee an identical primary position, so that the step of comparing the parameters determined in the upstream step and the parameters measured in the downstream step is carried out credibly, without introducing additional sources of errors. For this downstream step, posture is determined with the same means as those used in the upstream step, thus allowing the wearer to correct his posture in real time in order to make it identical to that adopted in the upstream step. A good means for achieving this consists in displaying the outline of the face on the screen overlaid on the real-time captured image and in displaying it in green when the person succeeds in making the measured outline correctly correspond with the real-time image.

In all the configurations described above, an additional step of reaching a decision on the fitting conformity of the piece of equipment may be performed automatically by means of a binary result of in-conformity/out-of-conformity type. In addition, to accentuate the user-friendly character of the method, this decision on the fitting conformity may possibly be displayed on a viewing screen, for example showing the face of the wearer with the frame and corrective eyeglasses matched with a colored shape, colored green if the fit is in conformity, or red if said fit is not in conformity.

In all the configurations described above, it is necessary to keep information, either numerical information such as for example the values of the fitting height and the positions of the ERCs, or information in the form of images or films of the face of the wearer in the primary gaze position, from the upstream step to the step of comparing the parameters determined in the upstream step and the parameters measured in the downstream step. An IT system will possibly be used to save and allow this information to be accessed. The information will be saveable and accessible by various opticians or various machines. A data format that will allow these data to be exchanged in a standardized way will advantageously be used. In other words, the results of the measurements relating to an individual will possibly serve to fill a database, which will possibly be accessible to an optician or to the wearer himself by means of the use of an access code taking the form of an identifier.

The invention claimed is:

1. A method for checking the fitting conformity of a piece of equipment comprising a frame and two corrective ophthalmic eyeglasses, comprising:
   (a) determining at least one parameter allowing the eyeglasses to be positioned in the frame and relative to the face of a wearer, wherein said determining comprises acquiring at least a first image of the face of the wearer with the frame without corrective eyeglasses;
   (b) acquiring at least a second image of the face of the wearer with the piece of equipment, wherein the second image comprises centering and horizontality reference marks, and wherein the second image is acquired by an identical measuring device in the same operating mode as the first image;
   (c) comparing the at least one parameter determined in step (a) and the second image;
   (d) reaching a decision on the fitting conformity of the piece of equipment;
   (e) validating conformity of the piece of equipment comprising the frame equipped with the corrective eyeglasses by integrating tolerance thresholds into the measurements; and
   (f) presenting validation of the conformity by comparison of at least one image of the face of the wearer with the corrective-eyeglass frame and at least one piece of information visible on said second image.

2. The checking method of claim 1, wherein step (a) and step (b) are carried out in different frames of reference, and wherein the method further comprises readjusting the at least one parameter prior to step (c).

3. The checking method of claim 1, further comprising checking the posture of the wearer between step (a) and step (b) to confirm that the relative positions between the piece of equipment and the wearer are substantially identical in step (a) and step (b).

4. The checking method of claim 1, wherein the parameter of step (c) applies to at least one geometricomorphological parameter chosen from height, pantoscopic angle, horizontality of the frame, horizontality of the eyeglasses relative to said frame, pupillary distance, face-form angle of said frame, and position of the centering reference marks on each of the eyeglasses.

5. The checking method of claim 1, further comprising consulting a database comprising the parameters determined in step (a) for an identified wearer and identified measuring equipment, the operating conditions under which said parameters were obtained, and the type of measuring equipment used, wherein the database is made accessible to each of the wearers by means of an identifier.

6. The checking method of claim 1, further comprising adjusting the measurement.

7. The checking method of claim 1, wherein steps (a) and (b) are carried out by the wearer with equipment equipped with a screen and connected to a telecommunications network.

8. The checking method of claim 7, wherein steps (b), (c), and (e) are carried out on a dedicated Internet site.

9. The checking method of claim 7, wherein steps (b), (c), and (e) are performed on the basis of a display on the screen during the capture of images and of an instruction indicating how to modify the wearer's posture with the aim of minimizing errors during step (c).

10. The checking method of claim 1, wherein step (d) comprises inspecting the position of distinctive reference marks on the corrective eyeglasses, wherein step (d) is performed with an individual wearing the fitted piece of equipment.

11. The checking method of claim 10, wherein the reference marks are crosses affixed to each eyeglass of the piece of equipment, wherein the crosses indicate the position of the eyes.

12. A checking device for carrying out the method of claim 1, said device comprising measuring equipment for determining at least one parameter in step (a), scaling equipment, inspecting equipment, comparing equipment, and equipment for displaying at least one piece of information on the validation of the fitting conformity of the frame.

13. The checking device of claim 12, further comprising a screen.

14. The checking device of claim 12, wherein the scaling equipment comprises at least one reference element of known size in said image.

* * * * *

UNITED STATES PATENT AND TRADEMARK OFFICE
CERTIFICATE OF CORRECTION

PATENT NO. : 10,234,700 B2  
APPLICATION NO. : 15/105225  
DATED : March 19, 2019  
INVENTOR(S) : Cécile Petignaud et al.

Page 1 of 1

It is certified that error appears in the above-identified patent and that said Letters Patent is hereby corrected as shown below:

On the Title Page

(73) Assignee:
Replace "ESSILOR INTERNATIONAL (COMPAGNIE GENERALE D'OPTIQUE)" with
-- ESSILOR INTERNATIONAL --.

Signed and Sealed this
Ninth Day of July, 2019

Andrei Iancu
*Director of the United States Patent and Trademark Office*